United States Patent [19]

Schaus et al.

[11] Patent Number: 5,637,624
[45] Date of Patent: Jun. 10, 1997

[54] RING-SUBSTITUTED 2-AMINO-1,2,3,4-TETRAHYDRONAPHTHALENES AND 3-AMINOCHROMANES

[75] Inventors: John M. Schaus; Robert D. Titus, both of Indianapolis, Ind.

[73] Assignee: Eli Lilly and Company, Indianapolis, Ind.

[21] Appl. No.: 28,642

[22] Filed: Mar. 9, 1993

Related U.S. Application Data

[63] Continuation of Ser. No. 739,597, Jul. 29, 1991, abandoned, which is a continuation of Ser. No. 315,752, Feb. 27, 1989, abandoned.

[51] Int. Cl.$^6$ .............. A61K 31/135; A61K 31/35; A61K 31/40; A61K 31/445
[52] U.S. Cl. .............. 514/657; 514/347; 514/351; 514/456; 546/294; 546/300; 549/404; 564/428
[58] Field of Search .............. 564/428; 514/657, 514/347, 456, 351; 546/294, 300; 549/404

[56] References Cited

U.S. PATENT DOCUMENTS

| | | | |
|---|---|---|---|
| 3,253,037 | 5/1966 | Huebner | 260/577 |
| 3,637,740 | 1/1972 | Sarges | 260/326.5 M |
| 3,758,640 | 9/1973 | Gittos et al. | 424/330 |
| 3,758,690 | 9/1973 | Gittos et al. | 424/330 |
| 3,929,891 | 12/1975 | Habig et al. | 260/580 |
| 5,026,787 | 6/1991 | Nixon et al. | 514/86 |

FOREIGN PATENT DOCUMENTS

| | | |
|---|---|---|
| 052932 | 6/1982 | European Pat. Off. . |
| 0272534 | 1/1988 | European Pat. Off. . |
| 272534 | 6/1988 | European Pat. Off. . |
| 1037014 | 7/1966 | United Kingdom . |
| WO81/03491 | 12/1981 | WIPO . |
| 8103491 | 12/1981 | WIPO . |
| WO87/02035 | 4/1987 | WIPO . |
| 8702035 | 4/1987 | WIPO . |
| WO88/04654 | 6/1988 | WIPO . |

OTHER PUBLICATIONS

Glennon, *J. Med. Chem.*, 30, 1–12 (1987).
DeMarinis et al., *J. Med. Chem.*, 25, 136–141 (1982).
Arvidsson et al., *J. Med. Chem.*, 24, 921–923 (1981).
Johansson et al., *J. Med. Chem.*, 28, 1049–1053 (1985).
*Organic Chemistry*, Morrison and Boyd, Allyn and Bacon, Inc., 1975, Sect. 7.9.
*Practical Catalytic Hydrogenation*, Morris Freifelder, John Wiley & Sons, 1971, pp. 438–440 and 490.
U.S. Patent Appl. Ser. No. 07/197,236 Feb. 10, 1989 Nixon et al.
Aridsson et al. II "8–Hydroxy–2–(di–n–propylamino) Titralin, Etc." *J. Med Chem.* 1981, 24, 921–923.
Aridsson et al. I "8–Hydroxy–2–(di–n–Propylamino) Titralin, Etc." *J. Med. Chem.* 1981, 24, 921–923.

*Primary Examiner*—Peter O'Sullivan
*Attorney, Agent, or Firm*—Robert D. Titus; Douglas J. Taylor

[57] ABSTRACT

The present invention provides novel ring-substituted 2-amino-1,2,3,4-tetrahydronaphthalenes and 3-aminochromanes which exhibit binding activity at the serotonin 1A receptor.

12 Claims, No Drawings

RING-SUBSTITUTED 2-AMINO-1,2,3,4-TETRAHYDRONAPHTHALENES AND 3-AMINOCHROMANES

This application is a continuation of application Ser. No. 07/739,597, filed on Jul. 29, 1991, now abandoned, which is a continuation of application Ser. No. 07/315,752, now abandoned, filed on Feb. 27, 1989.

BACKGROUND OF THE INVENTION

Over the last several years it has become apparent that the neurotransmitter serotonin (5-hydroxy-tryptamine—5-HT) is associated directly or indirectly with a number of physiological phenomena, including appetite, memory, thermoregulation, sleep, sexual behavior, anxiety, depression, and hallucogenic behavior [Glennon, R. A., *J. Med. Chem.* 30, 1 (1987)].

It has been recognized that there are multiple types of 5-HT receptors. These receptors have been classified as $5\text{-HT}_1$, $5\text{-HT}_2$, and $5\text{-HT}_3$ receptors, with the former being further divided into the sub-classes $5\text{-HT}_{1A}$, $5\text{-HT}_{1B}$, $5\text{-HT}_{1C}$, and $5\text{-HT}_{1D}$.

We have now discovered a class of compounds which exhibit high binding affinity at the $5\text{-HT}_{1A}$ receptor. The compounds, by reason of their $5\text{-HT}_{1A}$ agonist activity, are useful in the treatment, for example, of sexual dysfunction, anxiety, depression, and eating disorders, such as anorexia.

SUMMARY OF THE INVENTION

The present invention provides novel ring-substituted 2-amino-1,2,3,4-tetrahydronaphthalenes and 3-aminochromanes which are selective agonists at the $5\text{-HT}_{1A}$ receptor.

More specifically, this invention relates to a compound of the formula

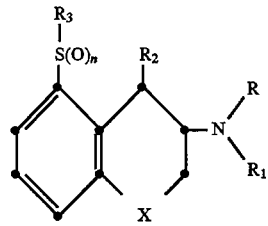

in which

R is $C_1$–$C_4$ alkyl, allyl, or cyclopropylmethyl;

$R_1$ is hydrogen, $C_1$–$C_4$ alkyl, allyl, cyclopropylmethyl, or aryl($C_1$–$C_4$-alkyl);

$R^2$ is hydrogen or methyl;

X is —$CH_2$— or —O—;

$R_3$ is $C_1$–$C_8$ alkyl, aryl, substituted aryl, aryl($C_1$–$C_4$-alkyl), substituted aryl($C_1$–$C_4$ alkyl), or $C_5$–$C_7$ cycloalkyl;

n is 0, 1, or 2;

and pharmaceutically acceptable acid addition salts thereof.

This invention also provides a pharmaceutical formulation which comprises, in association with a pharmaceutically acceptable carrier, diluent, or excipient, a compound of the formula

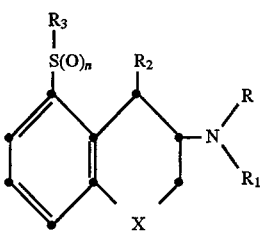

in which

R is $C_1$–$C_4$ alkyl, allyl, or cyclopropylmethyl;

$R_1$ is hydrogen, $C_1$–$C_4$ alkyl, allyl, cyclopropylmethyl, methyl, or aryl($C_1$–$C_4$-alkyl);

$R_2$ is hydrogen or methyl;

X is —$CH_2$— or —O—;

$R_3$ is $C_1$–$C_8$ alkyl, aryl, substituted aryl, aryl($C_1$–$C_4$-alkyl), substituted aryl($C_1$–$C_4$ alkyl), or $C_5$–$C_7$ cycloalkyl;

n is 0, 1, or 2;

and pharmaceutically acceptable acid addition salts thereof.

A further embodiment of the invention is a method for effecting a biological response at the $5\text{-HT}_{1A}$ receptor. More particularly, further embodiments are methods for treating a variety of disorders which have been linked to decreased activation of the $5\text{-HT}_{1A}$ site in mammals. Included among these disorders are anxiety, depression, sexual dysfunction, and eating disorders.

Any of these methods employ a compound of the formula

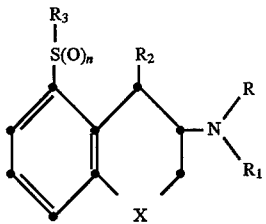

in which

R is $C_1$–$C_4$ alkyl, allyl, or cyclopropylmethyl;

$R_1$ is hydrogen, $C_1$–$C_4$ alkyl, allyl, cyclopropylmethyl, or aryl($C_1$–$C_4$-alkyl);

$R_2$ is hydrogen or methyl;

X is —$CH_2$— or —O—;

$R_3$ is $C_1$–$C_8$ alkyl, aryl, substituted aryl, aryl($C_1$–$C_4$-alkyl), substituted aryl($C_1$–$C_4$ alkyl), or $C_5$–$C_7$ cycloalkyl;

n is 0, 1, or 2;

and pharmaceutically acceptable acid addition salts thereof.

Another embodiment of this invention is a class of novel chromanes useful as intermediates in the production of certain of the compounds of this invention. These compounds have the formula

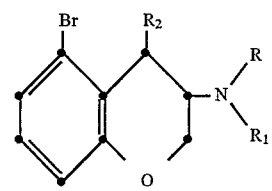

in which

R is $C_1$–$C_4$ alkyl, allyl, or cyclopropylmethyl;

$R_1$ is hydrogen, $C_1$–$C_4$ alkyl, allyl, cyclopropylmethyl, or aryl($C_1$–$C_4$-alkyl); and $R_2$ is hydrogen or methyl.

A further embodiment of this invention is a class of novel lithium intermediates useful in the production of compounds of this invention as well as a process using such intermediates.

The lithio compounds have the formula

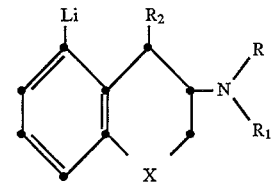

in which

R is $C_1$–$C_4$ alkyl, allyl, or cyclopropylmethyl;

$R_1$ is hydrogen, $C_1$–$C_4$ alkyl, allyl, cyclopropylmethyl, or aryl($C_1$–$C_4$-alkyl);

$R_2$ is hydrogen or methyl; and

X is —$CH_2$— or —O—.

The process aspect of this invention which employs the lithio intermediates is a process for producing a compound of the formula

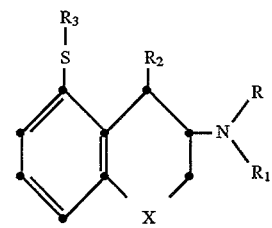

in which

R is $C_1$–$C_4$ alkyl, allyl, or cyclopropylmethyl;

$R_1$ is hydrogen, $C_1$–$C_4$ alkyl, allyl, cyclopropylmethyl, or aryl($C_1$–$C_4$-alkyl);

$R_2$ is hydrogen or methyl;

X is —$CH_2$— or —O—; and $R_3$ is $C_1$–$C_8$ alkyl, aryl, substituted aryl, aryl($C_1$–$C_4$-alkyl), substituted aryl($C_1$–$C_4$ alkyl), or $C_5$–$C_7$ cycloalkyl;

which comprises reacting a compound of the formula

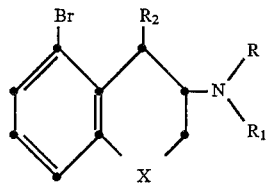

in which R, $R_1$, $R_2$, and X are as hereinabove defined, with an alkyl lithium to produce the corresponding 8-lithio compound, and reacting the 8-lithio compound with a compound of the formula $R_3$—S—S—$R_3$ in which $R_3$ is as hereinabove defined.

DETAILED DESCRIPTION OF THE INVENTION

In the above formulas, the term "$C_1$–$C_4$ alkyl" means a straight or branched alkyl chain having from one to four carbon atoms. Such $C_1$–$C_4$ alkyl groups are methyl, ethyl, n-propyl, isopropyl, n-butyl, isobutyl, sec-butyl, and t-butyl.

The term "aryl" means an aromatic structure whether carbocyclic or heterocyclic. Examples of such ring structures are phenyl, naphthyl, furyl, pyridyl, thienyl, and the like.

The aryl group may contain a ring substituent. Examples of typical ring substituents are $C_1$–$C_3$ alkyl, $C_1$–$C_3$ alkoxy, halo, hydroxy, $C_1$–$C_3$ thioalkyl, trifluoromethyl, and the like.

In the foregoing, the term "$C_1$–$C_3$ alkoxy" means any of methoxy, ethoxy, n-propoxy, and isopropoxy; the term "halo" means any of fluoro, chloro, bromo, and iodo; and the term "$C_1$–$C_3$ thioalkyl" means any of methylthio, ethylthio, n-propylthio, and isopropylthio.

While all of the compounds of the present invention are useful for treating a variety of disorders which have been linked to decreased activation of the 5-HT1A receptor in mammals, certain of the compounds are preferred. Thus, $R_2$ preferably is hydrogen.

R and $R_1$ preferably are both $C_1$–$C_4$ alkyl, and, more preferably, both are n-propyl. Also, n preferably is zero.

$R_3$ preferably is $C_1$–$C_8$ alkyl, substituted aryl, or substituted aryl($C_1$–$C_4$-alkyl), and, most preferably, methyl.

The compounds of the present invention possess an asymmetric carbon represented by the carbon atom labeled with an asterisk in the following formula:

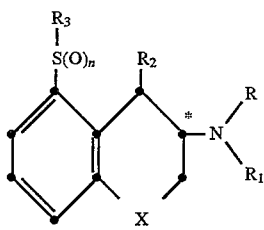

As such, each of the compounds exists as its individual d- and l-stereoisomers as well as the racemic mixture of such isomers. Accordingly, the compounds of the present invention include not only the dl-racemates but also their respective optically active d- and l-isomers.

In addition, when $R_2$ is methyl, a second asymmetric carbon, at the $R_2$ substituent, is present, giving rise to a further class of stereoisomers.

As mentioned hereinabove, the invention includes pharmaceutically acceptable acid addition salts of the compounds defined by the above formula. Since the compounds of this invention are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric phoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included as compounds of this invention.

The following compounds further illustrate compounds contemplated within the scope of this invention:

1-Methyl-2-(di-n-propylamino)-8-methylthio-1,2,3,4-tetrahydronaphthalene;
2-Ethylamino-8-ethylthio-1,2,3,4-tetrahydronaphthalene;
2-(N-Methyl-N-benzylamino)-8-methylthio-12,3,4-tetrahydronaphthalene;
2-Diallylamino-8-ethylthio-1,2,3,4-tetrahydronaphthalene;
1-Methyl-2-diethylamino-8-ethylsulfinyl-1,2,3,4-tetrahydronaphthalene;
1-Methyl-2-(di-n-propylamino)-8-ethanesulfonyl-1,2,3,4-tetrahydronaphthalene;
1-Methyl-2-benzylmethylamino-8-methylthio-1,2,3,4-tetrahydronaphthalene;
1-Methyl-2-(di-n-propylamino)-8-n-propylthio-1,2,3,4-tetrahydronaphthalene;
2-Dimethylamino-8-benzenesulfonyl-1,2,3,4-tetrahydronaphthalene;
2-(Di-cyclopropylmethylamino)-8-(p-toluenesulfonyl)1,2,3,4-tetrahydronaphthalene;
2-(Di-n-propylamino)-8-(p-chlorobenzenesulfonyl)-1,2,3,4-tetrahydronaphthalene;
2-Ethylamino-8-n-propylthio-1,2,3,4-tetrahydronaphthalene;
2-n-Butylamino-8-ethylthio-1,2,3,4-tetrahydronaphthalene;
2-(Di-n-propylamino)-8-n-octylthio-1,2,3,4-tetrahydronaphthalene;
2-(Di-n-propylamino)-8-methylthio-1,2,3,4-tetrahydronaphthalene;
3-(Di-n-propylamino)-5-methylthio-chromane; and the like.

The compounds of the present invention may be prepared by procedures well known to those of ordinary skill in the art. The compounds in which X is —CH₂ preferably are synthesized by preparation of an 8-bromo-2-tetralone. The 8-bromo-2-tetralone then is reductively aminated with the desired amine after which the bromo substituent is replaced with the desired thio substituent.

Schemes for these reactions are as follows:

A. Syntheses of 8-Bromo-2-tetralone and 8-Bromo-1-methyl-2-tetralone

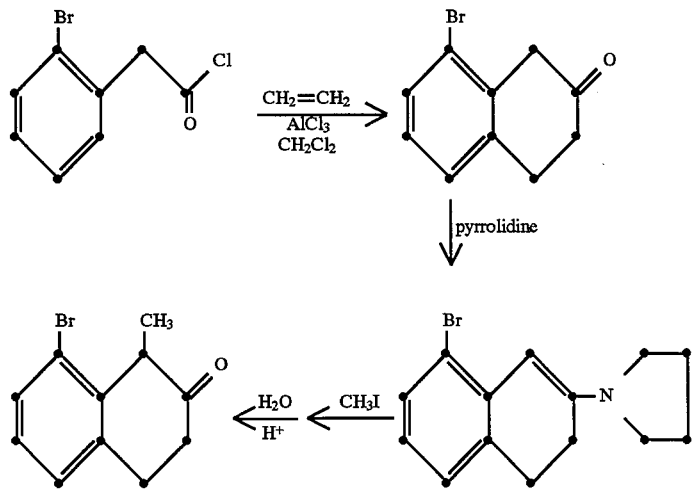

B. Reductive Amination

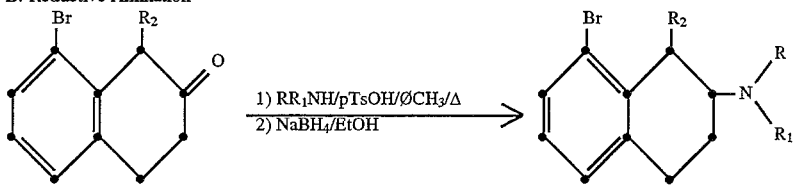

C. Replacement of Bromo Ring Substituent Via Lithiation

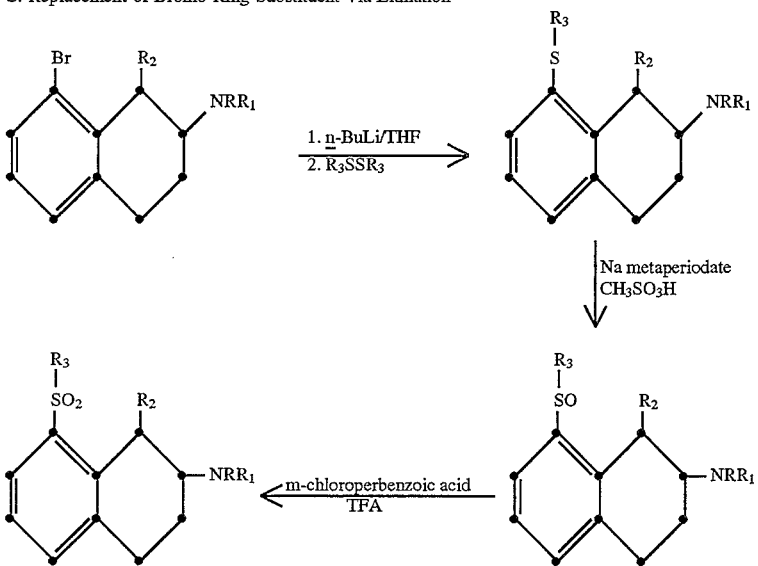

As depicted above, the 8-bromo-2-tetralones represent the intermediate which, when reductively aminated and treated with the appropriate disulfide, result in compounds of this invention and/or compounds useful as intermediates to the preparation of compounds of this invention.

The tetralones are available by any of a wide range of recognized methods. For example, they can be produced by a Friedel-Crafts reaction of an appropriately ring-substituted phenylacetyl chloride with ethylene in the presence of aluminum chloride.

When $R_2$ in the compounds of this invention is methyl, the methyl-substituted 8-bromo-2-tetralone can be prepared from the corresponding unsubstituted 8-bromo-2-tetralone. The 8-bromo-2-tetralone first is treated with pyrrolidine to produce the corresponding 1,2-dihydro-3-pyrrolidinyl-naphthalene. The latter, upon treatment with methyl iodide and acid hydrolysis, gives the desired 8-bromo-1-methyl-2-tetralone.

The tetralone, once formed, can, by simple reductductive amination using the selected amine, be converted to a 2-amino-8-bromo-1,2,3,4-tetrahydronaphthalene useful as an intermediate to a compound of this invention. The tetralone is first reacted with the amine to form the corresponding enamine after which the enamine is reduced with sodium borohydride to the tetrahydronaphthalene.

The 2-amino-8-bromo1,2,3,4-tetrahydronaphthalene is used to produce compounds of this invention by formation of a novel lithium intermediate via a lithiation reaction using an alkyl lithium, preferably n-butyllithium. The reactive lithium intermediate then is treated with an appropriate disulfide to produce the 8-thio compounds of this invention. Both the intermediates and the process are further aspects of this invention.

Alternatively, the 8-bromo-2-tetralone can first be protected and then lithiated and treated with the appropriate disulfide. The resulting 8-thio-2-tetralone, after deprotection, can then be reductively aminated to a compound of this invention.

The compounds of this invention in which X is oxygen are available by reductive amination and bromo replacement as in the foregoing, but using 5-bromo-3-chromanone. This molecule can be produced by a complex sequence of reactions beginning with m-bromophenol. The detailed reaction sequence is provided in the Examples following. Briefly, m-bromophenol is treated with allyl bromide in the presence of potassium carbonate to produce allyl 3-bromophenyl ether. The ether is converted to 2-allyl-3-bromophenol upon heating it in the presence of N,N-dimethylaniline. The phenol, upon reaction with ethyl chloroacetate, is converted to the ethyl ester of 2-allyl-3-(carboxymethoxy) bromobenzene. Upon oxidation using ozone followed by reductive work up, the allyl group is converted to a formyl-methyl substituent which is then further oxidized using Jones' Reagent to the carboxymethyl substituent, the resulting product being the ethyl ester of (2-carboxymethyl-3-bromo)phenoxyacetic acid. The partial ester is converted to the diethyl ester using ethanol and gaseous hydrogen chloride. In the presence of potassium t-butoxide, the diester is cyclized to a mixture of 4-ethoxycarbonyl-5-bromo-3-chromanone and 2-ethoxycarbonyl-5-bromo-3-chromanone. Upon heating the latter in the presence of acid, it is converted to 5-bromo-3-chromanone.

The 8-thio compounds, upon treatment with sodium metaperiodate, can be oxidized to the corresponding 8-sulfinyl compounds, also compounds of this invention. Additional compounds of this invention, the 8-sulfonyl compounds, are available by treatment of the 8-sulfinyl compounds with m-chloroperbenzoic acid.

The optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents are d- and l-tartaric acids, d- and l-ditoluoyltartaric acids, and the like.

Another aspect of this invention pertains to a particular method for producing optically active isomers of the compounds of this invention. As described above, the compounds of this invention generally and conveniently are produced via an 8-substituted-2-tetralone or a 5-substituted-3-chromanone. Either of these intermediates may be reductively alkylated with an optically active α-phenethylamine after which the resulting mixture of diastereomers is separated by recognized methodology, such as chromatography. Cleavage of the α-phenethyl moiety produces a correspondingly substituted, optically active 2-amino1,2,3,4-tetrahydronaphthalene or 3-aminochromane.

The conditions necessary for removing the phenethyl moiety are relatively severe and can tend to disrupt the integrity of the core tetralin or chromane molecule. It has been discovered that the cleavage can be carried out in a much more facile and efficient manner requiring only mild cleavage conditions when the particular α-phenethylamine which is used is p-nitro-α-phenethylamine. It is such a process that represents a further aspect of this invention.

Cleavage of the p-nitro-α-phenethyl moiety in accordance with the present invention is achieved by reduction of the p-nitro group followed by acid-catalyzed solvolysis of the resulting p-amino-α-phenethyl moiety. Reduction of the nitro group can be accomplished by a wide range of reducing agents including, for example, titanium trichloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the p-nitro-α-phenethyl moiety is hydrogenation of the amine monohydrochloride in methanol over a platinum catalyst.

Compounds highly useful as intermediates to the compounds of this invention are the corresponding 8-bromotetralins. It has been discovered that the 8-bromo compounds in their optically active form are not available using routine methodology whereas they can be prepared using the described method employing p-nitro-α-phenethylamine. Thus, a further aspect of this invention is directed to optically active 8-bromotetralins. These compounds have either of the following formulae

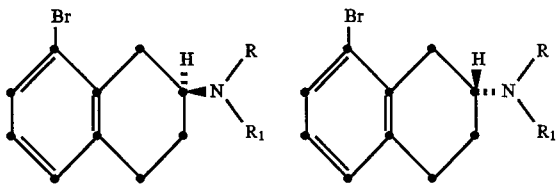

In the foregoing, R is hydrogen, $C_1$–$C_4$ alkyl, allyl, or cyclopropylmethyl; and $R_1$ is hydrogen, $C_1$–$C_4$ alkyl, allyl, cyclopropylmethyl, or aryl($C_1$–$C_4$-alkyl).

The compounds employed as initial starting materials in the synthesis of the compounds of this invention are well known and readily synthesized by standard procedures commonly employed by those of ordinary skill in the art.

The pharmaceutically acceptable acid addition salts of the invention are typically formed by reacting a 1,2,3,4-tetrahydronaphthalene or chromane of this invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods for their synthesis. The Examples are not intended to be limiting to the scope of the invention in any respect and should not be so construed.

Unless otherwise noted, the NMR data appearing in the following examples refers to the free bases of the subject compounds.

EXAMPLE 1

Preparation of 2-Di-n-propylamino-8-thiomethyl1,2,3,4-tetrahydronaphthalene.

A. 2-Di-n-propylamino-8-bromo1,2,3,4-tetrahydronaphthalene.

To a solution of 8-bromo-2-tetralone (3.0 gm, 13.3 mMol) in toluene (25 mL) were added di-n-propylamine (3.5 mL, 26 mMol) and p-toluenesulfonic acid (100 mg, 0.52 mMol). The reaction was heated to reflux, water being collected in a Dean-Stark trap. After four hours the reaction was concentrated in vacuo to give 8-bromo2-dipropylamino-3,4-dihydronaphthalene as a dark liquid which was immediately dissolved in methanol (50 mL) and acetic acid (5 mL). To this solution was then added sodium borohydride (2.0 gm, 52.9 mMol), and the mixture was stirred 18 hours at room temperature.

The reaction mixture was then diluted with 6N hydrochloric acid, stirred one hour at room temperature and then concentrated in vacuo. The residue was dissolved in water and washed once with diethyl ether. The remaining aqueous phase was made strongly basic with ammonium hydroxide and extracted well with dichloromethane. These organics were combined, dried ($Na_2SO_4$) and concentrated in vacuo to give the crude title compound as a dark oil. Purification by chromatography on basic alumina (dichloromethane) gave the product as a colorless oil. The hydrochloride salt was formed. Recrystallization (ethanol/diethyl ether) gave a colorless, crystalline solid (1.30 gm, 28%, m.p.=155° C.).

Alternatively, to the 8-bromo-2-dipropylamino-3,4-dihydronaphthalene (44.4 mMol) in tetrahydrofuran (100 ml) was added sodium cyano-borohydride (2.86 gm, 45.5 mMol) and the suspension was saturated with hydrogen chloride. After stirring for four hours the reaction mixture was poured into 15% aqueous sodium hydroxide (500 ml) and was stirred an additional two hours. This mixture was extracted with diethyl ether, and the ether extracts were combined, washed with water, washed with saturated aqueous sodium chloride, dried ($Na_2SO_4$) and concentrated in vacuo to give the crude title compound as a light orange oil. Purification by basic alumina chromatography (dichloromethane) gave the product as a light yellow oil (7.8 gm, 57%).

Analysis: Calculated for $C_{16}H_{24}NBr.HCl$: Theory: C, 55.42; H, 7.27; N, 4.04; Found: C, 55.53; H, 7.22; N, 3.84.

MS: 311(17), 309(16), 282(100), 280(100), 211(30), 209 (32), 130(92), 129(54), 128(40), 115(32), 72(43).

NMR (CDCl$_3$): 7.6–7.25(m, 1H), 7.2–6.9(m, 2H), 3.35–2.80(m, 5H), 2.80–2.40(m, 4H), 2.40–1.20(m, 6H), 1.19–0.80(t, J=7 Hz, 6H).

B. 2-Di-n-Propylamino-8-methylthio-1,2,3,4-tetrahydronaphthalene

To a solution of 8-bromo-2-di-n-propylamino-1,2,3,4-tetrahydronaphthalene (600 mg, 1.93 mMol) in tetrahydrofuran (20 mL) at −78° C. was added a solution of n-butyllithium in hexane (1.6M, 1.9 mL, 3.04 mMol). The solution was stirred at −78° C. for one hour, forming a light orange solution. Dimethyl disulfide (0.24 mL, 3.00 mMol) was added, and the reaction mixture was allowed to warm gradually to room temperature. The colorless solution was diluted with water and extracted with dichloromethane. The dichloromethane extracts were combined, dried (Na$_2$SO$_4$), and concentrated in vacuo to give the crude product as a light yellow oil. Purification by flash chromatography (3% methanol in dichloromethane+tr. NH$_4$OH) gave the product as a colorless, viscous oil (430 mg, 80%). The hydrochloride salt was formed. Recrystallization (ethanol/diethyl ether) gave a colorless, crystalline solid (m.p.=185° C.).

Analysis: Calculated for C$_{17}$H$_{27}$NS.HCl: Theory: C, 65.04; H, 8.99; N, 4.46; Found: C, 65.25; H, 9.13; N, 4.47.

MS: 277(31), 251(10), 250(29), 248(100), 177(90), 132 (15), 130(69), 128(50), 127(48).

NMR (CDCl$_3$): 7.13–6.68(m, 3H), 3.20–2.68(m, 4H), 2.62–2.33(m, 4H), 2.44(s, 3H), 2.12–1.81(m, 1H), 1.72–1.20(m, 6H), 1.00–0.86 (6, J=7 Hz, 6H).

EXAMPLE 2

Preparation of 2-Di-n-propylamino-8-thioethyl-1,2,3,4-tetrahydronaphthalene.

Using the procedure described in Example 1, 8-bromo-2-di-n-propylamino-1,2,3,4-tetrahydronaphthalene (930 mg, 3.0 mMol) was reacted with diethyl disulfide (0.40 mL, 3.3 mMol) to give the crude title compound as a light yellow oil. Purification by flash chromatography (33% diethyl ether in hexane +tr. NH$_4$OH) gave the desired product as a colorless oil (650 mg, 74%). The fumarate salt was formed. Recrystallization (ethanol/diethyl ether) gave a colorless, crystalline solid (m.p.=105°–107° C.).

Analysis: Calculated for C$_{18}$H$_{29}$NS.C$_4$H$_4$O$_4$: Theory: C, 62.09; H, 8.28; N, 2.83; Found: C, 61.87; H, 8.42; N, 3.11.

MS: 292(3), 290(16), 281(2), 280(8), 278(29), 250(18), 249(11), 207(5), 134(26), 119(10), 74(56), 59(88), 44(78).

NMR (CDCl$_3$): 7.08–6.72(m, 3H), 3.24–2.70(m, 6H), 2.70–2.36(m, 4H), 2.16–1.86(m, 1H), 1.76–1.20(m, 9H), 1.08–0.76(t, J=7 Hz, 6H).

EXAMPLE 3

Preparation of 2-Di-n-propylamino-8-thiophenyl-1,2,3,4-tetrahydronaphthalene.

Using the procedure described in Example 1, 8-bromo-2-di-n-propylamino-1,2,3,4-tetrahydronaphthalene (930 mg, 3.0 mMol) was reacted with diphenyl disulfide (720 mg, 3.3 mMol) to give the title compound as a colorless oil. The fumarate salt was formed. Recrystallization (acetone/diethyl ether) gave colorless crystals (270 mg, 20%, m.p.= 133°–135° C.).

Analysis: Calculated for C$_{22}$H$_{29}$NS.C$_4$H$_4$O$_4$: Theory: C, 68.54; H, 7.30; N, 3.07;

Found: C, 68.37; H, 7.24; N, 3.09.

MS: 339(16), 311(7), 310(25), 309(100), 239(24), 237 (22), 161(28), 130(35), 129(40), 128(35).

NMR (CDCl$_3$): 7.18(s, 5H), 7.04–6.80(m, 3H), 3.08–2.72 (m, 4H), 2.32–2.27(m, 4H), 2.11–1.63(m, 1H), 1.63–1.18 (m, 6H), 1.04–0.68(t, J=7 Hz, 3H).

EXAMPLE 4

Preparation of 2-Di-n-propylamino-8-thiobenzyl- 1,2,3,4-tetrahydronaphthalene.

Using the procedure described in Example 1, 8-bromo-2-di-n-propylamino1,2,3,4-tetrahydronaphthalene (930 mg, 3.0 mMol) was reacted with dibenzyl disulfide (840 mg, 3.3 mMol) to give the crude title compound as a light yellow oil. Purification by flash chromatography (3% methanol in dichloromethane+tr. NH$_4$OH) gave the desired product as a colorless oil (630 mg, 60%). The maleate salt was formed. Recrystallization (ethanol/diethyl ether) gave a colorless, crystalline solid (m.p.=137°–138.5° C.).

Analysis: Calculated for C$_{23}$H$_{31}$NS.C$_4$H$_4$O$_4$: Theory: C, 69.05; H, 7.51; N, 2.98; Found: C, 69.28; H, 7.47; N, 2.86.

MS: 353(10), 325(17), 324(63), 262(21), 253(8), 203(10), 161(10), 129(25), 127(19), 91(100).

NMR (CDCl$_3$): 7.32–6.68(m, 8H), 4.06(s, 2H), 3.16–2.62 (m, 4H), 2.62–2.24(m, 4H), 2.16–1.80(m, 1H), 1.71–1.18 (m, 6H), 1.08–0.72(t, J=7 Hz), 6H).

EXAMPLE 5

Preparation of 2-Di-n-propylamino-8-methylsulfinyl-1,2,3,4-tetrahydronaphthalene.

To a solution of water (60 mL) which contains methanesulfonic acid (0.16 mL, 2.33 mMol) was added 2-di-propylamino-8-methylthio-1,2,3,4-tetrahydronaphthalene (630 mg, 2.33 mMol). To this solution was added a solution of sodium metaperiodate (550 mg, 2.57 mMol) in water (10 mL), and the reaction mixture was stirred for two days at room temperature. The reaction mixture was made basic (NH$_4$OH) and extracted with dichloromethane. The organic extracts were combined, dried (Na$_2$SO$_4$) and concentrated in vacuo to give the crude title compound as a light yellow oil. Purification by flash chromatography (3% methanol in dichloromethane+tr. NH$_4$OH) gave the desired product (580 mg, 85%) as a colorless oil. The fumarate salt was formed. Recrystallization (ethanol/diethyl ether) gave a colorless, crystalline solid which was found to be extremely hygroscopic. Drying in a vacuum dessicator (60° C., 18 hours) gave a colorless glass (260 mg, m.p. =63° C.).

Analysis: Calculated for C$_{17}$H$_{27}$NOS.C$_4$H$_4$O$_4$: Theory: C, 61.59; H, 7.63; N, 3.42; Found: C, 61.38; H, 7.48; N, 3.57.

MS: 294(3), 293(4), 291(1), 278(10), 277(14), 276(60), 266(12), 265(33), 264(100), 250(7), 249(28), 248(8), 193 (46).

NMR (CDCl$_3$): 7.80–7.76(m, 1H), 7.36–7.00(m, 2H), 3.28–2.20(m, 8H), 2.76–2.62(d, J=3 Hz, 3H), 2.20–1.85(m, 1H), 1.80–1.20(m, 6H), 1.04–0.72(t, J=7 Hz, 6H).

EXAMPLE 6

Preparation of 2-Di-n-propylamino-8-methylsulfonyl-1,2,3,4-tetrahydronaphthalene.

To a solution of 2-dipropylamino-8-methylsulfinyl-1,2,3,4-tetrahydronaphthalene (350 mg, 1.19 mMol) in trifluoroacetic acid (20 ml) was added a solution of metachloroperbenzoic acid (80%, 518 mg, 2.38 mMol) in trifluoroacetic acid (5 mL). The solution was stirred at room temperature for 18 hours and poured over ice. The resulting mixture was made basic (NH$_4$OH) and extracted well with dichloromethane. The organic extracts were combined, dried (NA$_2$SO$_4$) and concentrated in vacuo to give the crude title compound as a brown oil. Purification by flash chromatography (3% methanol in dichloromethane+tr. NH$_4$OH) gave the desired product as a light orange oil (110 mg, 30%). The maleate salt was formed. Recrystallization (ethanol/diethyl ether) gave a colorless solid (70 mg, m.p.=113°–114° C.).

Analysis: Calculated for C$_{17}$H$_{27}$NO$_2$S.C$_4$H$_4$O$_4$: Theory: C, 59.27; H, 7.34; N, 3.29; Found: C, 59.19; H, 7.35; N, 3.18.

MS: 309(3), 283(1), 282(8), 281(18), 280(100), 209(11), 130(45).

NMR (CDCl$_3$): 7.88–7.76(dd, J=3 Hz, 7 Hz, 1H), 7.36–7.12(m, 2H), 3.20–2.78(m, 4H), 3.08(s, 3H), 2.64–2.38(m, 4H), 2.20–1.84(m, 1H), 1.80–1.14(m, 6H), 1.08–0.86(t, J=7 Hz, 6H).

EXAMPLE 7

Preparation of 2-Dimethylamino-8-thiomethyl-1,2,3,4-tetrahydronaphthalene.

A. 2-Dimethylamino-8-bromo-1,2,3,4-tetrahydronaphthalene.

To a solution of 8-bromo-2-tetralone (4.5 gm, 20 mMol) in acetonitrile (100 mL) were added sodium acetate (9.9 gm, 120 mMol), sodium cyanoborohydride (880 mg, 120 mMol), dimethylamine hydrochloride (9.8 gm, 120 mMol) and 4A sieves (2.0 gm). The mixture was stirred at room temperature for 3 days. The reaction mixture was then filtered through a bed of celite, and the filtrate was poured into a slurry of ice and water.

The solution was made acidic (HCl) and extracted well with diethyl ether. The remaining aqueous was made basic (NH$_4$OH) and extracted well with dichloromethane. These organic phases were combined, dried (NA$_2$SO$_4$), and concentrated in vacuo to give a dark oil. Purification by flash chromatography (5% methanol in dichloromethane+tr. NH$_4$OH) gave the title compound as a yellow oil (1.5 gm, 30%).

MS: 257(2), 256(10), 255(42), 254(18), 253(42), 252(8), 240(7), 238(8), 174(13), 130(18), 129(40), 128(24) 115(20), 103(21), 84(43), 71(100), 70(68).

NMR (CDCl$_3$): 7.55–7.18(m, 1H), 7.16–6.85(m, 2H), 3.2–2.43(m, 6H), 2.4(s, 6H), 2.0–1.8(m, 1H).

B. 2-Dimethylamino-8-thiomethyl-1,2,3,4-tetrahydronaphthalene.

To a solution of 2-Dimethylamino-8-bromo-1,2,3,4-tetrahydronaphthalene (760 mg, 3 mMol) in tetrahydrofuran (20 mL) at −78° C. was added n-butyllithium in hexane (1.6M, 3.0 mL, 4.8 mMol). The solution was stirred at −78° C. for one hour. To the solution was then added dimethyl disulfide (0.33 mL, 4.1 mMol), and the resulting mixture was allowed to warm to room temperature. The light yellow solution was diluted with water, made acidic (HCl), and extracted well with diethyl ether. The remaining aqueous was made basic (NH$_4$OH) and extracted well with dichloromethane. These organics were combined, dried (Na$_2$SO$_4$), and concentrated in vacuo to give a light yellow oil. Purification by flash chromatography (3% methanol in dichloromethane+tr. NH$_4$OH) gave the desired compound as a light yellow oil (420 mg, 63%). The hydrochloride salt was formed. Recrystallization (acetone/diethyl ether) gave a colorless, crystalline solid (m.p.=170° C.).

Analysis: Calculated for C$_{13}$H$_{19}$NS.HCl: Theory: C, 60.56; H, 7.82; N, 5.43; Found: C, 60.87; H, 7.94; N, 5.43.

MS: 223(4), 222(10), 221(100), 220(6), 219(1), 206(9), 177(33), 71(52).

NMR (CDCl$_3$): 7.2–6.8(m, 3H), 3.05–2.48(m, 5H), 2.45 (s, 3H), 2.40(s, 6H), 2.15–2.00(m, 1H), 1.7–1.5(m, 1H).

EXAMPLE 8

Preparation of cis-1-Methyl-2-di-n-propylamino-8-thiomethyl-1,2,3,4-tetrahydronaphthalene.

A. 1-Methyl-8-bromo-2-tetralone.

To a solution of 8-bromo-2-tetralone (10 gm, 44.4 mMol) in toluene (175 ml) was added pyrrolidine (6.6 ml), and the solution was stirred at reflux for three hours. The volatiles were removed in vacuo to give 8-bromo-3-pyrrolidino-1,2-dihydronaphthalene as a brown oil. To this oil in p-dioxane (60 mL) was added methyl iodide (20 mL, 322 mMol), and the resulting solution was stirred at reflux for eighteen hours. The reaction mixture was diluted with water (60 mL) and acetic acid (3.2 mL), and heating was continued for an additonal three hours. After this time the solution was cooled to room temperature and the volatiles removed in vacuo. The residue was suspended in water and extracted well with diethyl ether. The organic phases were combined, washed with saturated aqueous NaHCO$_3$, dried with Na$_2$SO$_4$ and concentrated in vacuo to give an orange oil. Purification by flash chromatography (33% diethyl ether in hexane) gave the title compound as a light orange oil (6.88 gm, 65%).

NMR (CDCl$_3$): 7.48–7.28(m, 1H), 7.20–6.80(m, 2H), 4.0–3.67(q, J=7.2 Hz, 1H), 3.40–2.16(m, 4H), 1.48–1.28(d, J=7.2 Hz, 3H).

B. cis-1-Methyl-2-n-propylamino-8-bromo-1,2,3,4-tetrahydronaphthalene.

To a solution of 8-bromo-1-methyl-2-tetralone (4.05 gm, 16.9 mMol) in dichloromethane (60 mL) were added magnesium sulfate (3.0 gm, 25 mMol) and n-propylamine (2.0 mL, 24.4 mMol). The mixture was stirred at room temperature for twenty hours. The reaction mixture was filtered through a bed of celite and the filtrate concentrated in vacuo to give 1-methyl-2-n-propylimino-8-bromo-1,2,3,4- tetrahydronaphthalene as a dark residue.

NMR (CDCl$_3$): 7.56–7.24(m, 1H), 7.20–6.80(m, 2H), 4.20–3.88(q, J=7.2 Hz, 1H), 3.56–2.0(m, 6H), 1.88–1.52 (sextet, J=5.4 Hz, 2H), 1.44–1.32(d, J=7.2 Hz, 3H), 1.16–0.84(t, J=5.4 Hz, 3H).

To a solution of the preceding dark residue in tetrahydrofuran (60 mL) were added sodium cyanoborohydride (1.8 gm, 29 mMol), and the solution was saturated with hydrogen chloride. The resulting mixture was stirred for eighteen hours at room temperature. The reaction mixture was then poured into cold water (200 mL), made strongly basic (NaOH), and stirred for two hours. The reaction mixture was then made acidic (HCl) and extracted well with diethyl ether. The remaining aqueous phase was made basic (NH$_4$OH) and extracted well with dichloromethane. These organic phases were combined, dried (Na$_2$SO$_4$), and concentrated in vacuo to give a light yellow oil. Purification by flash chromatography (20% hexane in diethyl ether+tr. NH$_4$OH) gave the title compound as a colorless oil (1.47 gm, 31%).

NMR (CDCl$_3$): 7.4–7.19(m, 1H), 7.04–6.78(m, 2H), 3.60–3.08(m, 1H), 3.00–2.41(m, 1.90–1.35(m, 4H), 1.35–0.70(m, 8H).

(The trans-isomer of the title compound was also isolated as a colorless oil (680 mg, 14%)).

C. cis-1-Methyl-2-di-n-propylamino-8-bromo-1,2,3,4-tetrahydronaphthalene.

To a solution of cis-1-Methyl-2-n-propylamino-8- bromo-1,2,3,4-tetrahydronaphthalene (1.47 gm, 5.2 mMol) in acetonitrile (30 mL) were added 1-iodopropane (.59 mL, 5.8 mMol) and proton sponge (2.2 gm, 10.4 mMol), and the mixture was stirred at 50° C. for eighteen hours. The colorless suspension was filtered and the filtrate concentrated in vacuo to give a light yellow oil. Purification by flash chromatography (20% diethyl ether in hexane+tr. NH$_4$OH) gave the desired compound as a colorless glass (330 mg, 20%).

NMR (CDCl$_3$): 7.40–7.15(dd, J=3.2 Hz, 7.2 Hz, 1H), 7.0–6.68(m, 2H), 3.50–3.12(m, 1H), 3.0–2.0(m, 6H), 2.0–1.68(m, 2H), 1.68–1.20(m, 5H), 1.20–1.04(d, J=7.2 Hz, 3H), 1.00–0.72(t, J=5.4 Hz, 6H).

D. cis-1-Methyl-2-di-n-propylamino-8-thiomethyl-1,2,3,4-tetrahydronaphthalene.

To a solution of cis-1-Methyl-2-n-dipropylamino-8-bromo-1,2,3,4-tetrahydronaphthalene (330 mg, 1.02 mMol) in tetrahydrofuran (10 mL) at −78° C. were added n-butyl-lithium in hexane (1.6M, 1.1 mL, 1.8 mMol), and the solution was stirred at −78° C. for one hour. To the yellow solution was added dimethyl disulfide (.11 mL, 1.22 mMol), and the solution was allowed to warm to room temperature. The now colorless solution was poured into water, made acidic (HCl), and extracted well with diethyl ether. The remaining aqueous phase was made basic (NH$_4$OH) and extracted well with dichloromethane. These organic extracts were combined, dried (Na$_2$SO$_4$), and concentrated in vacuo to give a colorless oil. Purification by flash chromatography (20% diethyl ether in hexane +tr. NH$_4$OH) gave the desired compound as a colorless, viscous oil (240 mg, 81%). The hydrobromide salt was formed. Recrystallization (acetone/hexane) gave a colorless crystalline solid (m.p.=149°–150° C.).

Analysis: Calculated for C$_{18}$H$_{29}$NS.HBr: Theory: C, 58.05; H, 8.12; N, 3.76; Found: C, 57.84; H, 8.12; N, 3.92.

MS: 293(1), 292(3), 291(10), 290(2), 266(1), 265(6), 264(20), 262(100) 192(10), 191(65), 151(25), 144(66), 115(28), 72(42).

NMR (CDCl$_3$): 7.16–6.66(m, 3H), 3.56–3.12(m, 1H), 3.00–2.44(m, 6H), 2.40(s, 3H), 2.00–1.68(m, 2H), 1.68–1.19(m, 5H), 1.19–1.10(d, J=7.2 Hz, 3H), 1.00–0.70(t, J=7.2 Hz, 6H).

EXAMPLE 9

Preparation of (R)-2-Di-n-propylamino-8-thiomethyl-1,2,3,4-tetrahydronaphthalene and (S)-2-Di-n-propylamino-8-thiomethyl-1,2,3,4-tetrahydronaphthalene.

A. N-[1-(4'-Nitrophenyl)ethyl]-N-(8-bromo-2-tetralin)-amine.

A solution of 50 g of Na$_2$CO$_3$ in 300 mL of water was used to convert 66 g (0.30 mol) of the hydrochloride salt of (S)-(−)-α-methyl-4'-nitrobenzylamine to its free base. The free base was extracted into CH$_2$Cl$_2$. This solvent was then removed under vacuum, and the residue was dissolved in 700 mL of acetonitrile. To this solution were added successively 4.5 mL (0.08 mol) of HOAc, 4.9 g (0.08 mol) of NaCNBH$_3$, 65 g (0.29 mol) of 8-bromo-2-tetralone, and 20 g of 3A molecular sieves. The mixture was stirred under nitrogen for 16 h. Another 31.4 g (0.50 mol) of NaCNBH$_3$ was added, followed by 13.5 mL (0.24 mol) of HOAc. After 4 more hours an addition of 2 mL of HOAc was made, followed at two hour intervals by two more such additions. After stirring for another 16 h the mixture was filtered, and most of the acetonitrile was removed under vacuum. The residual mixture was poured into cold Na$_2$CO$_3$ solution and extracted with CH$_2$Cl$_2$. The extract was washed with NaCl solution and dried over Na$_2$SO$_4$. The CH$_2$Cl$_2$ was evaporated leaving the crude product as a viscous brown oil. The crude product was taken up in 300 mL of ether and then extracted into a solution of 50 g of tartaric acid in 1.5 L of 30% methanol in water. The aqueous layer was washed twice with fresh ether, then basified with sat. Na$_2$CO$_3$ solution and extracted into CH$_2$Cl$_2$. This extract was washed with NaCl solution and dried over Na$_2$SO$_4$. Removal of the solvent under vacuum gave 84.9 g (78% yield) of the product as an amber oil which appeared to be clean by NMR.

B. N-[1-(4'-Nitrophenyl)ethyl]-N-(8-bromo-2-tetralin) propionamides.

The compound from Part A (84.9 g, 0.23 mol) was dissolved in 1 L of CH$_2$Cl$_2$. This solution was treated with 71 mL (0.51 mol) of triethylamine and then slowly with 42 mL (0.48 mol) of propionyl chloride. The mixture was stirred for 16 h. It was then treated with cold Na$_2$CO$_3$ solution. After stirring vigorously for three hours, the CH$_2$Cl$_2$ layer was separated. This solution was washed with aqueous tartaric acid solution and then with Na$_2$CO$_3$ solution. After drying over Na$_2$SO$_4$, the CH$_2$Cl$_2$ was evaporated leaving 101 g of the crude diastereomeric mixture of amides. The diastereomers were separated by chromatographing in 20–30 g runs on an HPLC system that employed columns containing about 400 g of silica gel ("Prep 500"). The solvent system was a gradient proceeding from pure toluene to 20% EtOAc in toluene. The total weight of the first diastereomer (S,R) from the column was 49.6 g. The second diastereomer (S,S) weighed 40.6 g. Both diastereomers were viscous oils. Both contained about 2% toluene. A satisfactory analysis was obtained for the S,S diastereomer after rigorous drying of a small sample. Slightly high carbon and low bromine percentages in the sample of the S,R diastereomer suggested that a trace of solvent had persisted even after drying. Yields of the two diastereomers were approximately 48% and 40%, respectively.

(S,R)-Diastereomer:

OR: $[\alpha]_D^{25}$+9.4° (C=10.MeOH)

Analysis: Calculated for C$_{21}$H$_{23}$BrN$_2$O$_3$: Theory: C, 58.48; H, 5.38; N, 6.49; Br, 18.53; Found: C, 60.07; H, 5.61; N, 6.28; Br, 17.76.

MS 433(1), 431(1), 361(3), 359(3), 210(100), 208(100), 129(67), 57(54).

UV (EtOH): $\lambda_{max}$271 nm (ε9600)

IR (CHCl$_3$): $\lambda_{max}$1642 cm$^{-1}$ (S,S)-Diastereomer:

OR: $[\alpha]_D^{25}$−114° (C=10 MeOH)

Analysis: Calculated for C$_{21}$H$_{23}$BrN$_2$O$_3$: Theory: C, 58.48; H, 5.38; N, 6.49; Br, 18.53; Found: C, 58.66; H, 5.43; N, 6.37; Br, 18.33.

MS: 433(1), 431(1), 361(5), 359(5), 210(100), 208(100), 129(99), 57(92).

UV (EtOH): $\lambda_{max}$273 nm (ε9000)

IR (CHCl$_3$): $\lambda_{max}$1642 cm$^{-1}$

C. (S,R)-N-[1-(4'-Nitrophenyl)ethyl]-N-(8-bromo-2-tetralin)-1-propylamine.

A solution of 49 g (0.114 mol) of the S,R-diastereomer from Part B in 200 mL of THF was added gradually to 230 mL of ice cooled 1M borane in THF. The solution was then refluxed under nitrogen for 2 h. After the solution was allowed to cool, it was carefully treated with 100 mL of MeOH. This solution was stirred for 1 h. The solvents were evaporated under vacuum, and the residue was taken up in a mixture of 250 mL of DMSO and 30 mL of water. This solution was heated on a steam bath for 1 h. It was then cooled and extracted with $CH_2Cl_2$. The extracts were washed with NaCl solution and dried over $Na_2SO_4$. The $CH_2Cl_2$ was evaporated, and the crude free base was converted to its HCl salt by dissolving in 1 L of ether and adding 50 mL of 2.6M HCl in ether. The salt was collected and washed with fresh ether. The dried salt, which weighed 50.4 g (97% yield), analyzed satisfactorily.

OR: $[\alpha]_D^{25}+28°$ (C=10 MeOH)

Analysis: Calculated for $C_{21}H_{25}BrN_2O_2 \cdot HCl$: Theory: C, 55.58; H, 5.78; N, 6.17; Cl, 7.81; Br, 17.61; Found: C, 55.32; H, 5.94; N, 5.97; Cl, 7.61; Br, 17.33.

MS: 418(14), 416(15), 389(73), 387(71), 240(61), 238 (68), 130(100), 104(59).

UV (EtOH): $\lambda_{max}$ 267 nm ($\epsilon$10,000)

D. (S,S)-N-[1-(4'-Nitrophenyl)ethyl]-N-(8-bromo-2-tetralin)propylamine.

The reduction procedure described in Part C was used to reduce 40 g (0.093 mol) of the S,S diastereomer of the analogous amide. Elemental analysis indicated that the crude HCl salt, obtained in 98% yield, was slightly impure.

OR: $[\alpha]_D^{25}-94°$ (C=10, MeOH)

Analysis: Calculated for $C_{21}H_{25}BrN_2O_2 \cdot HCl$: Theory: C, 55.58; H, 5.78; N, 6.17; Found: C, 55.13; H, 5.94; N, 5.69.

MS: 418(21), 416(20), 389(79), 387(78), 240(54), 238 (57), 130(100), 104(74).

UV (EtOH): $\lambda_{max}$ 269 nm ($\epsilon$10,000)

E. (R)-8-Bromo-2-(N-propylamino)tetralin.

A solution of 12.5 g (27.6 mmol) of the HCl salt from Part C (S,R diastereomer) in 200 mL of MeOH was hydrogenated for 8 h at 40 psi over 0.5 g of sulfided 5% platinum on carbon. After filtering off the catalyst, most of the MeOH was evaporated under vacuum without heat. Thorough ether washing of the methanolic slurry that remained afforded 6.55 g (78% yield) of the HCl salt of the title compound. A satisfactory analysis was obtained without without further purification.

OR: $[\alpha]_D^{25}+54°$ (C=8, MeOH)

Analysis: Calculated for $C_{13}H_{18}BrN \cdot HCl$: Theory: C, 51.25; H, 6.29; N, 4.60; Br, 26.23; Cl, 11.64;

Found: C, 51.48; H, 6.41; N, 4.47; Br, 26.25; Cl, 11.63.

MS: 269(24), 267(23), 240(63), 238(66), 211(30), 209 (34), 130(85), 56(100).

NMR (DMSOd$_6$): $\delta$0.97 (t, 3H), 1.71 (sextet, 2H), 1.79 (sextet, 1H), 2.27 (broad d, 1H), 2.75 (qt, 1H), 2.88 (broad t, 2H), 2.96 (mult, 2H), 3.25 (qt, 1H), 3.48 (broad mult, 1H), 7.12 (t, 1H), 7.18 (d, 1H), 7.49 (d, 1H), 9.19 (broad s, 2H).

F. (S)-8-Bromo-2-(N-propylamino)tetralin.

Hydrogenation of the HCl salt of the S,S diastereomeric amine from Part D in a manner analogous to that described above gave a 94% yield of the HCl salt of the title compound. In this case the crude product showed minor impurities. A small sample was recrystallized from i-PrOH for analysis.

OR: $[\alpha]_D^{25}-54°$ (C=10, MeOH)

Analysis: Calculated for $C_{13}H_{18}BrN \cdot HCl$: Theory: C, 51.25; H, 6.29; N, 4.60; Br, 26.23; Cl, 11.64; Found: C, 51.31; H, 6.30; N, 4.41; Br, 26.44; Cl, 11.81.

MS: 269(24), 267(23), 240(63), 238(66), 211(30), 209 (34), 130(85), 56(100).

NMR (DMSOd$_6$): $\delta$0.97 (t, 3H), 1.71 (sextet, 2H), 1.79 (sextet, 1H), 2.27 (broad d, 1H), 2.75 (qt, 1H), 2.88 (broad t, 2H), 2.96 (mult, 2H), 3.25 (qt, 1H), 3.48 (broad mult, 1H), 7.12 (t, 1H), 7.18 (d, 1H), 7.49 (d, 1H), 9.19 (broad s, 2H).

G. (S)-8-Bromo-N,N-dipropyl-2-aminotetralin.

To a solution of (S)-8-Bromo-N-propyl-2-amino-tetralin (5.0 gm, 18.6 mMol) as produced in Part F in acetonitrile (75 mL) were added n-propyl iodide (3.0 mL, mMol), followed by powdered potassium carbonate (4.0 gm, 29 mMol), and the reaction mixture was stirred for the weekend at 50° C. The reaction mixture was then cooled to room temperature and filtered. The filtrate was concentrated in vacuo to give a yellow oil. Purification by flash chromatography (2:1 hexane:diethyl ether +tr. NH$_4$OH) gave the title compound as a colorless oil (3.6 gm, 62%).

NMR (CDCl$_3$): $\delta$7.39(d, J=8.01 Hz, 1H), 6.98(m, 2H), 2.90(m, 4H), 2.53(m, 5H), 2.02(m, 1H), 1.50(m, 5H), 0.91(t, J=7.30 Hz, 6H).

H. (R)-8-Bromo-N,N-dipropyl-2-aminotetralin.

(R)-8-Bromo-N-propyl-2-aminotetralin (10.5 gm, 39.2 mMol) as produced in Part E was treated as described in Part G to give the title compound as a colorless oil (9.6 gm, 80%). The NMR spectrum recorded for this compound was identical to the spectrum recorded for the compound of Part G.

I. (S)-8-Thiomethyl-N,N-dipropyl-2-aminotetralin hydrochloride.

To a solution of (S)-8-Bromo-N,N-dipropyl-2-aminotetralin (16.4 gm, 52.9 mMol) from Part G in tetrahydrofuran (400 mL) at −78° C. were added a solution of n-butyllithium in hexane (1.6M, 39.7 mL, 63.5 mMol), and the solution was allowed to stir at this temperature for 1.5 hours. To the solution were then added dimethyl disulfide (9 mL, 100 mMol), and the reaction mixture was allowed to warm gradually to room temperature. The reaction mixture was then diluted with water and made acidic with 10% hydrochloric acid. The aqueous mixture was then extracted once with diethyl ether and the ether phase discarded. The remaining aqueous was made strongly basic with ammonium hydroxide and then was extracted well with dichloromethane. The organic extracts were combined, washed with saturated aqueous sodium chloride, dried over sodium sulfate, and concentrated in vacuo to give a yellow oil. purification by flash chromatography (2:1 hexane:diethyl ether+tr. NH$_4$OH) gave a light yellow oil. This oil in diethyl ether was converted to the hydrochloride salt. Crystallization (ethanol/diethyl ether) gave the title compound as a colorless, crystalline solid (11.7 gm, 70%, m.p.= 178.5°–180° C.).

OR: $[\alpha]_D^{20}$ (H$_2$O)=−65.14°

Analysis: Calculated for $C_{17}H_{27}NS \cdot HCl$: Theory: C, 65.04; H, 8.99; N, 4.46; Found: C, 65.32; H, 9.13; N, 4.48.

MS: 278(6), 277(19), 250(7), 249(20), 248(100), 179(18), 178(23), 177(67), 130(47), 129(39), 128(32).

NMR(CDCl$_3$) $\delta$7.13(t, J=9 Hz, 1H), 7.00(d, J=9 Hz, 1H), 6.90(d, J=9 Hz, 1H), 2.95(m, 4H), 2.50(m, 5H), 2.48(s, 3H), 2.03(m, 1H), 1.54(m, 5H), 0.92(t, J=6 Hz, 6H).

J. (R)-8-Thiomethyl-N,N-dipropyl-2-aminotetralin hydrochloride.

(R)-8-Bromo-N,N-dipropyl-2-aminotetralin (17 gm, 54.8 mMol) from Part H was treated as described in Part I to give the title compound as a colorless, crystalline solid (10.5 gm, 61%, m.p.=177.5°–178.5° C.).

OR: $[\alpha]_D^{20}$(H$_2$O)=+64.85°

Analysis: Calculated for $C_{17}H_{27}NS \cdot HCl$: Theory: C, 65.04; H, 8.99; N, 4.46; Found: C, 65.32; H, 9.02; N, 4.50.

EXAMPLE 10

Preparation of 3-(Di-n-propylamino)-5-methylthio-chromane hydrochloride.

A. Allyl 3-bromophenyl ether.

The title compound was synthesized in 91% yield from 3-bromophenol by the procedure described in *Journal of Organic Chemistry*, 26, 3631, (1961).

B. 2-Allyl-3-bromophenol.

The title compound was synthesized from allyl 3-bromophenyl ether by an ortho Claisen rearrangement in dimethylaniline as described in *Helvetica Chemica Acta*, 56(1), 14, (1973).

C. 2-Allyl-3-(carboxymethoxy)bromobenzene.

To a solution of the product from Part B (15.2 gm, 71.4 mMol) in acetonitrile (350 mL) were added ethyl chloroformate (9.6 gm, 78.5 mMol) and potassium carbonate (19.7 gm, 143 mMol). The reaction mixture was stirred at 60° C. for 66 hours. After this time the reaction mixture was filtered and concentrated in vacuo to give the crude product as a light yellow oil. Purification by flash chromatography (1:1 hexane:diethyl ether) gave the desired compound as a colorless oil (16.6 gm, 78%).

NMR(CDCl$_3$): $\delta$7.22(d, J=8.05 Hz, 1H), 7.03(t, J=8.12 Hz, 1H), 6.70(d, J=8.26 Hz, 1H), 6.00(m, 1H), 5.02(m, 2H), 4.64(s, 2H), 4.27(q, J=7.22 Hz, 2H), 3.67 (d, J=6.25 Hz, 2H), 1.30(t, J=7.08 Hz, 3H).

D. 2-Formylmethyl-3-(carboxymethoxy)bromobenzene.

A solution of the product from Part C (16.6 gm, 55.5 mMol) in absolute ethanol (500 mL) was cooled to −78° C., and then ozone was bubbled into the reaction mixture. After 20 minutes the solution had become light blue and all of the starting material had been consumed (TLC 1:1 hexane:diethyl ether). The reaction mixture was allowed to warm gradually to room temperature. At this point a colorless solid had precipitated, and the suspension was again cooled to −78° C. Dimethyl sulfide (7.3 mL, 100 mMol) was added dropwise, and then the reaction mixture was allowed to warm gradually to room temperature. Volatiles were removed in vacuo to give the title compound as a light yellow oil (18.3 gm, 100+%).

IR(thin film): 1022.5, 1073.1, 1189.7, 1203.7, 1725.4, 1754.7cm$^{-1}$.

MS(FD): 302(100), 300(90).

NMR(CDCl$_3$): $\delta$9.70(s, 1H), 7.25(d, J=8.06 Hz, 1H), 7.11(t, J=8.16 Hz, 1H), 6.74(d, J=8.13 Hz, 1H), 4.62(s, 2H), 4.22(q, J=7.14 Hz, 2H), 4.00(s, 2H), 1.26(t, J=6.81 Hz, 3H).

E. 2-Carboxymethyl-3-(ethoxycarbonylmethoxy)bromobenzene.

To approximately 55 mMol of crude product from Part D in acetone (300 mL) were added Jones' Reagent until a bright orange color persists in solution. A dark green solid formed as the temperature gradually increased to reflux. Isopropanol was added to destroy any excess chromium trioxide, and then the reaction mixture was diluted with water and then extracted well with diethyl ether. The ether phases were combined and then washed well with water. The remaining ether phase was extracted three times with saturated aqueous sodium bicarbonate (100 mL). These extracts were then made strongly acidic with hydrochloric acid (10%) and extracted well with chloroform:isopropanol (3:1). The combined organic extracts were then washed with saturated aqueous sodium chloride, dried over sodium sulfate and concentrated in vacuo to give the title compound as a yellow viscous oil (12.3 gm, 71%).

IR(thin film): 1191.1, 1205.8, 1278.8, 1449.3, 1465.3, 1574.6, 1171.1, 1739.3, 1754.8 cm$^{-1}$.

MS(FD): 318(100), 316(90).

NMR(CDCl$_3$): $\delta$7.26(d, J=8.14 Hz, 1H), 7.12(t, J=8.17 Hz, 1H), 6.75(d, J=8.12 Hz, 1H), 4.66(s, 2H), 4.25(q, J=6.84 Hz, 2H), 4.04(s, 2H), 1.29(t, J=7.22 Hz, 3H).

F. 2-Carboxymethyl-3-(carboxymethoxy)bromobenzene, diethyl ester.

A solution of the product from Part E (12.3 gm, 38.8 mMol) in absolute ethanol (400 mL) was saturated with hydrogen chloride, and the solution was allowed to stir for 18 hours at room temperature. Volatiles were removed in vacuo to give a light brown oil. Purification by flash chromatography (1:1 hexane:diethyl ether) gave the desired compound as a colorless oil (12.4 gm, 93%).

NMR(CDCl$_3$): $\delta$7.24(d, J=8.09 Hz, 1H), 7.10(t, J=8.53 Hz, 1H), 6.73(d, J=8.13 Hz, 1H), 4.63(s, 2H), 4.21(m, 4H), 3.97(s, 2H), 1.27(m, 6H).

G. Mixture of 4-Ethoxycarbonyl-5-bromo-3-chromanone and 2-ethoxycarbonyl-5-bromo-3-chromanone.

A solution of the diester from Part F (6 gm, 17.4 mMol) in tetrahydrofuran (50 ml) was added dropwise to a solution of potassium t-butoxide (3.90 gm, 34.8 mMol) in tetrahydrofuran (200 mL). The reaction mixture was then immediately poured over ice and the solution made acidic with 10% hydrochloric acid. The mixture was then extracted well with diethyl ether. The organic phases were combined, washed with saturated aqueous sodium chloride, dried over sodium sulfate, and concentrated in vacuo to give a yellow solid. Purification by flash chromatography (1:1 hexane:diethyl ether) gave two compounds. 2-Ethoxycarbonyl-5-bromo-3-chromanone was recovered as colorless crystals (1.3 gm).

NMR(CDCl$_3$): $\delta$7.25(d, J=8.10Hz, 1H), 7.05(m, 2H), 4.42(q, J=6.84 Hz, 2H), 3.70(s, 2H), 1.58(br s, 1H), 1.42(t, J=7.10 Hz, 3H).

The 4-ethoxycarbonyl-5-bromo-3-chromanone was recovered as a light yellow viscous oil (1.7 gm).

NMR(CDCl$_3$): $\delta$7.26(d, J=8.14 Hz, 1H), 7.18(t, J=8.18 Hz, 1H), 7.04(d, J=8.12 Hz, 1H), 4.90(s, 1H), 4.75(d, J=16 Hz, 1H), 4.22(m, 3H), 1.27(t, J=7.05 Hz, 3H).

Total yield for cyclized product was 3.0 gm (58%).

H. 5-Bromo-3-chromanone.

A suspension of 2-ethoxycarbonyl-5-bromo-3-chromanone (300 mg, 1 mMol) in methanol (5 mL) and 10% hydrochloric acid (3 mL) was heated at reflux for 2 hours. All of the solid had not dissolved; therefore, trifluoroacetic acid (1 mL) was added, and heating was continued for 18 hours. The reaction mixture was diluted with water and extracted well with diethyl ether. The ether phases were combined, dried over sodium sulfate, and concentrated in vacuo to give a yellow glass. Purification by flash chromatography (1:1 hexane:ether) gave the title compound as a light yellow glass (120 mg, 53%).

NMR(CDCl$_3$): $\delta$7.32(d, J=8.08 Hz, 1H), 7.12(t, 8.19 Hz, 1H), 7.02(d, J=8.05 Hz, 1H), 4.41(s, 2H), 3.69(s, 1H).

I. 5-Bromo-3-di-n-propyl-3-aminochromane.

To a solution of the product from Part H (620 mg, 2.73 mMol) in toluene (20 mL) were added dipropylamine (0.7 mL, 6 mMol) and p-toluenesulfonic acid (100 mg, 0.52 mMol), and the mixture was heated at reflux with constant water removal (Dean-Stark trap). After 3 hours the reaction mixture was cooled to room temperature and the volatiles removed in vacuo to give a dark reddish-orange residue. This material was dissolved in tetrahydrofuran (40 mL), sodium cyanoborohydride (400 mg, 6.4 mMol) was added and the solution was saturated with hydrogen chloride. The reaction mixture was stirred for 18 hours at room temperature. The reaction mixture was then poured into 15% sodium hydroxide (100 mL) and was stirred vigorously for 2 hours.

The reaction mixture was then extracted well with diethyl ether. The organic phases were combined, dried over sodium sulfate, and concentrated in vacuo. The residue was suspended in 10% hydrochloric acid and the aqueous extracted once with diethyl ether. This ether extract was discarded and the remaining aqueous made basic with concentrated ammonium hydroxide and then extracted well with dichloromethane. The combined organics were washed with saturated aqueous sodium chloride, dried over sodium sulfate, and concentrated in vacuo to give a light yellow oil. Purification by flash chromatography (4:1 hexane:diethyl ether+ tr. $NH_4OH$) gave the title compound as a colorless oil (420 mg, 50%).

NMR($CDCl_3$): δ7.16(d, J=7.77 Hz, 1H), 6.98(t, J=7.85 Hz, 1H), 6.80(d, J=8.16 Hz, 1H), 4.28(m, 1H), 3.78(t, J=8.30 Hz, 1H), 3.17(m, 1H), 2.93(m, 1H), 2.67(m, 1H), 2.53(t, J=7.42 Hz, 4H), 1.49(sextet, J=7.32 Hz, 4H), 0.91(t, J=7.28 Hz, 6H).

J. 3-Di-n-propyl-amino-5-thiomethyl-chromane hydrochloride.

To a solution of the product from Part I (420 mg, 1.35 mMol) in tetrahydrofuran (25 mL) at −78° C. was added a solution of n-butyllithium in hexane (1.6M, 2 mL, 3.2 mMol), and the resulting solution was stirred at −78° C. for 1 hour. To the mixture was then added dimethyl. disulfide (0.25 mL, 2.5 mMol), and the reaction mixture allowed to warm gradually to room temperature. The reaction mixture was diluted with water and made acidic with hydrochloric acid. The aqueous was then extracted well with diethyl ether, and the ether extracts were discarded. The remaining aqueous was made basic with concentrated ammonium hydroxide and extracted well with dichloromethane. The organics were dried over sodium sulfate and concentrated in vacuo to give a colorless less oil. Purification by flash chromatography (1:1 hexane:diethyl ether+tr. $NH_{40}H$) gave a colorless, viscous oil (290 mg, 77%). The hydrochloride salt was formed. Recrystallization (ethanol/diethyl ether) gave the title compound as colorless crystals (m.p.=181°–183° C.).

Analysis: Calculated for $C_1H_{25}NOS \cdot HCl$: Theory: C, 60.83; H, 8.30; N, 4.43; Found: C, 61.09; H, 8.32; N, 4.44.

MS: 280(6), 279(28), 252(8), 251(23), 250(100), 179(7), 98(50).

NMR($CDCl_3$): δ7.10(t, J=8.01 Hz, 1H), 6.75(d, J=7.89 Hz, 1H), 6.63(d, J=7.97 Hz, 1H), 4.30(m, 1H), 3.78(t, J=8.30 Hz, 1H), 3.20(m, 1H), 2.89(m, 1H), 2.56(m, 5H), 2.45(s, 3H), 1.48(sextet, J=7.32 Hz, 4H), 0.91(t, J=7.31 Hz, 6H).

As noted above, the compounds of this invention have agohist binding affinity for the 5-$HT_{1a}$ receptor. Therefore, another embodiment of the present invention is a method of effecting agonist action at the 5-$HT_{1a}$ receptors which comprises administering to a mammal in need thereof a pharmaceutically effective amount of a compound of the invention.

The term "pharmaceutically effective amount", as used herein, represents an amount of a compound of the invention which is capable of binding to serotonin 1a receptors. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal. A special feature of the compounds of this invention is that they are extremely selective in effecting agonist action at serotonin 1A receptors relative to other serotonin receptors.

A variety of physiologic functions have been shown to be subject to influence by brain serotonergic neural systems. As such, the compounds of this invention are believed to have the ability to treat in mammals a variety of 5-HT mediated states and disorders such as sexual disorders, eating disorders, depression, alcoholism, pain, senile dementia, anxiety, and smoking. Therefore, the present invention also provides methods of treating the above disorders at rates set forth above for agonist action in mammals at 5-HT receptors.

The following experiment was conducted to demonstrate the ability of the compounds of the present invention to effect agonist action at the serotonin 1a receptors. This general procedure is set forth in Wong et al., *J. Neural Transm.* 71:207–218 (1988).

Male Sprague-Dawley rats (110–150 g) from Harlan Industries (Cumberland, Ind.) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000×g for 10 min and then at 17000×g for 20 min, a crude synaptosomal fraction was sedimented. The pellet was suspended in 100 vol of 50 mM Tris-HCl, pH 7.4, incubated at 37° C. for 10 min, and centrifuged at 50000×g for 10 min. The process was repeated and the final pellet was suspended in ice-chilled 50 mM Tris-HCl, pH 7.4. By the radioligand binding method, sites specifically labeled by tritiated 8-hydroxy-2-dipropylamino1,2,3,4-tetrahydronaphthalene ($^3$H-8-OH-DPAT) have been identified as 5-$HT_{1A}$ receptors.

Binding of (hu 3H-8-OH-DPAT) was performed according to the previously described method [Wong et. al., *J. Neural Transm.* 64:251–269 (1985)]. Briefly, synaptosomal membranes isolated from cerebral cortex were incubated at 37° C. for 10 min. in 2 ml of 50 mM Tris-HCl, pH 7.4; 10 µM pargyline; 0.6 mM ascorbic acid; and 0.4 nM $^3$H-8-OH-DPAT. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 µM was also included in separate samples to establish nonspecific binding. Specific binding of $^3$H-8-OH-DPAT is defined as the difference of radioactivity bound in the absence and in the presence of 10 µM unlabeled 8-OH-DPAT.

The results of the evaluation of various compounds of the present invention are set forth below in Table I. In Table I, the first column provides the Example Number of the compound evaluated; the next 6 columns identify the structure of the compound evaluated when taken with the formula set forth in the heading; the next-succeeding column identifies the salt form of the compound evaluated; and the final column provides the amount of the test compound expressed in nanomolar concentration required to inhibit the binding of $^3$H-8-OH-DPAT) by 50%, and is indicated in Table I as $IC_{50}$.

TABLE I

BINDING AT 5HT$_{1a}$ IN VITRO

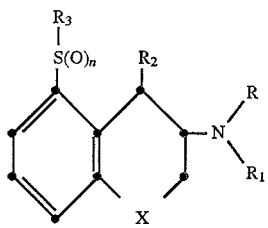

| Compound of Example No. | R | R$_1$ | R$_2$ | R$_3$ | n | X | Salt Form | IC$_{50}$ (nM) 5HT$_{1a}$ |
|---|---|---|---|---|---|---|---|---|
| 1 | Pr | Pr | H | CH$_3$ | 0 | CH$_2$ | hydrochloride | 0.3 |
| 2 | Pr | Pr | H | CH$_2$CH$_3$ | 0 | CH$_2$ | fumarate | 30.7 |
| 3 | Pr | Pr | H | phenyl | 0 | CH$_2$ | fumarate | 22.2 |
| 4 | Pr | Pr | H | benzyl | 0 | CH$_2$ | maleate | 2.8 |
| 5 | Pr | Pr | H | CH$_3$ | 1 | CH$_2$ | fumarate | 71.1 |
| 6 | Pr | Pr | H | CH$_3$ | 2 | CH$_2$ | maleate | 10 |
| 7 | CH$_3$ | CH$_3$ | H | CH$_3$ | 0 | CH$_2$ | hydrochloride | 21 |
| 8 | Pr | Pr | CH$_3$ | CH$_3$ | 0 | CH$_2$ | hydrobromide | 297 |
| 9 | Pr | Pr | H | p-tolyl | 0 | CH$_2$ | oxalate | 59 |
| 10 | Pr | Pr | H | 2-pyridyl | 0 | CH$_2$ | oxalate | 9 |
| 11 | Pr | Pr | H | CH$_3$ | 0 | O | hydrochloride | 2.5 |

The activity of compounds of this invention when administered orally was determined and compared with literature compounds structurally related to the compounds of this invention. Thus, the test compound was administered to male Sprague-Dawley rats orally (p.o.), five rats being used in each test group. The rats were sacrificed two hours following p.o. administration, and the brain concentration of 5-hydroxyindoleacetic acid (5-HIAA), a metabolite of 5-HT, was measured. The decrease in brain concentration of 5-HIAA is presented in Table II following.

TABLE II

Effectiveness of Compounds by Oral Administration

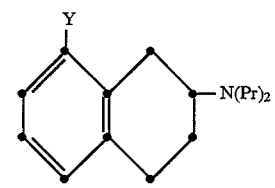

| Y | Dose, mg/Kg | 5-HIAA Concentration in Whole Brain, nmoles/g | Percent Reduction over Control |
|---|---|---|---|
| — | 0 | 1.67 ± 0.08 | — |
| OH | 0.1 | 1.62 ± 0.07 | 0 |
| OH | 1 | 1.75 ± 0.05 | 0 |
| OH | 10 | 1.40 ± 0.06 | 16 |
| SCH$_3$ | 0.1 | 1.56 ± 0.04 | 0 |
| SCH$_3$ | 1 | 1.45 ± 0.03 | 13 |
| SCH$_3$ | 10 | 1.25 ± 0.06 | 25 |

From the foregoing, it appears that the minimum effective dose for the hydroxy compound (8-OH-DPAT) when administered orally is about 10 mg/kg whereas for the compound of this invention (Y=SCH$_3$) the minimum effective fective dose is about ten-fold less, i.e., about 1 mg/kg.

These results are to be distinguished from the minimum effective doses of the compounds when administered subcutaneously (s.c.). The 8-OH-DPAT appears to be effective at about 0.03 mg/kg whereas the compound of this invention (Y=SCH$_3$) is about ten-fold less potent, the minimum effective dose being about 0.3 mg/kg.

The compounds of this invention are preferably formulated prior to administration. Therefore, another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard getatin capsules are prepared using the following ingredients:

|  | Quantity (mg/capsule) |
|---|---|
| 2-di-n-propylamino-8-methylthio-1,2,3,4-tetrahydronaphthalene hydrochloride dihydrate | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| 2-di-n-propylamino-8-methylthio-1,2,3,4-tetrahydronaphthalene hydrochloride | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| 2-diisopropylamino-8-methylsulfinyl-1,2,3,4-tetrahydronaphthalene dihydrochloride | 0.25 |
| ethanol | 29.75 |
| Propellant 22 | 70.00 |
| (chlorodifluoromethane) |  |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  |  |
|---|---|
| 2-methylethylamino-8-phenylthio-1,2,3,4-tetrahydronaphthalene maleate | 60 mg |
| starch | 45 mg |
| microcrystalline cellulose | 35 mg |
| Polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  |  |
|---|---|
| 2-propylamino-8-phenylsulfonyl-1,2,3,4-tetrahydronaphthalene hydrochloride | 80 mg |
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

|  |  |
|---|---|
| 1-methyl-2-di-n-propylamino-8-benzylthio-1,2,3,4-tetrahydronaphthalene hydrochloride | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2-diallylamino-8-p-toluylthio-1,2,3,4-tetrahydronaphthalene hydrochloride | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| 2-diethylamino-8-methylsulfinyl-1,2,3,4-tetrahydronaphthalene hydrochloride | 100 mg |
| isotonic saline | 1000 ml |

The solution of the above ingredients generally is administered intravenously at a rate of 1 ml per minute to a subject suffering from depression.

We claim:

1. A compound of the formula

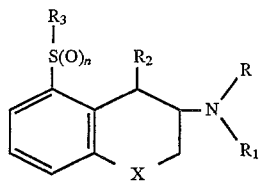

in which R is $C_1$–$C_4$ alkyl, allyl, or cyclopropylmethyl;

$R_1$ is hydrogen, $C_1$–$C_4$ alkyl, allyl, or cyclopropylmethyl;

$R_2$ is hydrogen or methyl;

X is —$CH_2$—;

$R_3$ is $C_1$–$C_8$ alkyl, phenyl, phenyl substituted with $C_1$–$C_3$ alkyl, $C_1$–$C_3$ alkoxy, halo, hydroxy, $C_1$–$C_3$ alkylthio or trifluoromethyl, pyridyl, pyridyl substituted with $C_1$–$C_3$ alkyl, $C_1$–$C_3$ alkoxy, halo, hydroxy, $C_1$–$C_3$ alkylthio or trifluoromethyl, phenyl $C_1$–$C_4$ alkyl, phenyl $C_1$–$C_4$ alkyl substituted on the phenyl ring with $C_1$–$C_3$ alkyl, $C_1$–$C_3$ alkoxy, halo, hydroxy, $C_1$–$C_3$ alkylthio or trifluoromethyl;

n is 0, 1 or 2;

and pharmaceutically acceptable acid addition salts thereof.

2. Compound of claim 1, in which n is zero.

3. Compound of claim 2, in which $R_2$ is hydrogen.

4. Compound of claim 3, in which R and $R_1$, are both $C_1$–$C_4$ alkyl.

5. Compound of claim 4, in which $R_3$ is $C_1$–$C_8$ alkyl.

6. Compound of claim 5, in which R and $R_1$, are both n-propyl.

7. Comppound of claim 6, in which $R_3$ is methyl.

8. A pharmaceutical formulation which comprises, in association with a pharmaceutically acceptable carrier, diluent, or excipient, an effective amount of a compound of the formula

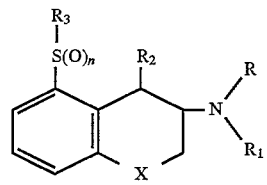

in which

R is $C_1$–$C_4$ alkyl, allyl, or cyclopropylmethyl;

$R_1$ is hydrogen, $C_1$–$C_4$ alkyl, allyl, or cyclopropylmethyl;

$R_2$ is hydrogen or methyl;

X is —$CH_2$—;

$R_3$ is $C_1$–$C_8$ alkyl, phenyl, phenyl substituted with $C_1$–$C_3$ alkyl, $C_1$–$C_3$ alkoxy, halo, hydroxy, $C_1$–$C_3$ alkylthio or trifluoromethyl, pyridyl, pyridyl substituted with $C_1$–$C_3$ alkyl, $C_1$–$C_3$ alkoxy, halo, hydroxy, $C_1$–$C_3$ alkylthio, or trifluoromethyl, phenyl $C_1$–$C_4$ alkyl, phenyl $C_1$–$C_4$ alkyl substituted on the phenyl ring with $C_1$–$C_3$ alkyl, $C_1$–$C_3$ alkoxy, halo, hydroxy, $C_1$–$C_3$ alkylthio or trifluoromethyl;

n is 0, 1 or 2;

and pharmaceutically acceptable acid addition salts thereof.

9. Formulation of claim 8, in which the compound is 2-di-n-propylamino-8-methylthio-1,2,3,4-tetrahydronaphthalene or a pharmaceutically acceptable acid addition salt thereof.

10. A compound of the formula

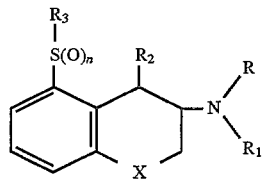

in which

R is $C_1$–$C_4$ alkyl, allyl, or cyclopropylmethyl;

$R_1$ is hydrogen, $C_1$–$C_4$ alkyl, allyl, or cyclopropylmethyl;

$R_2$ is hydrogen or methyl;

X is —O—;

$R_3$ is $C_1$–$C_8$ alkyl, phenyl, phenyl substituted with $C_1$–$C_3$ alkyl, $C_1$–$C_3$ alkoxy, halo, hydroxy, $C_1$–$C_3$ alkylthio or trifluoromethyl, pyridyl, pyridyl substituted with $C_1$–$C_3$ alkyl, $C_1$–$C_3$ alkoxy, halo, hydroxy, $C_1$–$C_3$ alkylthio, or trifluoromethyl, phenyl $C_1$–$C_4$ alkyl, phenyl $C_1$–$C_4$ alkyl substituted on the phenyl ring with $C_1$–$C_3$ alkyl, $C_1$–$C_3$ alkoxy, halo, hydroxy, $C_1$–$C_3$ alkylthio or trifluoromethyl;

n is 0, 1 or 2;

and pharmaceutically acceptable acid addition salts thereof.

11. Compound of claim 10 which is 3-(di-n-propylamino)-5-methylthiochromane.

12. A pharmaceutical formulation which comprises, in association with a pharmaceutically acceptable carrier, diluent or excipient, an effective amount of a compound of claim 10.

* * * * *